(12) United States Patent
Rudzinski et al.

(10) Patent No.: US 10,799,139 B2
(45) Date of Patent: Oct. 13, 2020

(54) METHOD AND SYSTEM FOR EEG SIGNAL PROCESSING

(71) Applicants: Maciej Rudzinski, Warsaw (PL); Marek Rudzinski, Warsaw (PL)

(72) Inventors: Maciej Rudzinski, Warsaw (PL); Marek Rudzinski, Warsaw (PL); Adrian Elczewski, Warsaw (PL)

(73) Assignees: Maciej Rudzinski, Warsaw (PL); Marek Rudzinski, Warsaw (PL)

( * ) Notice: Subject to any disclaimer, the term of this patent is extended or adjusted under 35 U.S.C. 154(b) by 363 days.

(21) Appl. No.: 15/505,229

(22) PCT Filed: Aug. 19, 2015

(86) PCT No.: PCT/EP2015/069080
§ 371 (c)(1),
(2) Date: Feb. 20, 2017

(87) PCT Pub. No.: WO2016/026907
PCT Pub. Date: Feb. 25, 2016

(65) Prior Publication Data
US 2017/0273585 A1 Sep. 28, 2017

(30) Foreign Application Priority Data

Aug. 22, 2014 (PL) .......................... 409241

(51) Int. Cl.
*A61B 5/048* (2006.01)
*A61B 5/04* (2006.01)
(Continued)

(52) U.S. Cl.
CPC .......... *A61B 5/048* (2013.01); *A61B 5/04014* (2013.01); *A61B 5/0478* (2013.01);
(Continued)

(58) Field of Classification Search
CPC ... A61B 5/048; A61B 5/04014; A61B 5/0478; A61B 5/0488; A61B 5/167;
(Continued)

(56) References Cited

U.S. PATENT DOCUMENTS

2007/0276278 A1* 11/2007 Coyle .................. A61B 5/0476
600/529
2012/0296569 A1 11/2012 Shahaf et al.
2015/0011907 A1* 1/2015 Purdon ................ A61B 5/0478
600/544

FOREIGN PATENT DOCUMENTS

KR 2012-0105095 A 9/2012

OTHER PUBLICATIONS

International Search Report and Written Opinion of the International Searching Authority for International Patent Application No. PCT/EP2015/069080 dated Sep. 26, 2016, 15 pgs.
(Continued)

*Primary Examiner* — Matthew Kremer
*Assistant Examiner* — Avery M Foley
(74) *Attorney, Agent, or Firm* — Merchant & Gould P.C.

(57) ABSTRACT

A method for processing EEG signals includes reading the EEG signals from two frontal electrodes of an electroencephalograph (301); converting the EEG signals to a frequency domain (305); determining values of a BIS/BAS response on the basis of an asymmetry between the EEG signals (208). The method includes calculating the asymmetry between the EEG signals in the frequency domain in a frequency range from 26 to 29 Hz.

14 Claims, 8 Drawing Sheets

(51) Int. Cl.
    *A61B 5/00*           (2006.01)
    *A61B 5/16*           (2006.01)
    *A61B 5/0478*       (2006.01)
    *A61B 5/0488*       (2006.01)

(52) U.S. Cl.
    CPC ............ *A61B 5/0488* (2013.01); *A61B 5/167* (2013.01); *A61B 5/6815* (2013.01); *A61B 5/721* (2013.01); *A61B 5/7207* (2013.01); *A61B 5/7257* (2013.01)

(58) Field of Classification Search
    CPC ..... A61B 5/6815; A61B 5/7207; A61B 5/721; A61B 5/7257; A61B 5/163
    See application file for complete search history.

(56) References Cited

OTHER PUBLICATIONS

John, E.R., "Principles of Neurometrics", American Journal of EEG Technology, 30(4): 251-266 (1990).

Paquette, V. et al., "Effect of a psychoneurotherapy on brain electromagnetic tomography in individuals with major depressive disorder", Psychiatry Research: Neuroimaging, 174(3): 231-239 (2009).

Sutton, S.K. et al., "Prefrontal brain asymmetry: A biological substrate of the behavioural approach and inhibition systems", 8(3): 204-210 (1997).

* cited by examiner

METHOD AND SYSTEM FOR EEG SIGNAL PROCESSING

This application is a National Stage Application of PCT/EP2015/069080, filed 19 Aug. 2015, which claims benefit of Serial No. P.409241, filed 22 Aug. 2014 in Poland, and which applications are incorporated herein by reference. To the extent appropriate, a claim of priority is made to each of the above disclosed applications.

FIELD OF INVENTION

This disclosure is related to a computer-implemented method and system for EEG signal processing. In particular, it is related to a method that allows correct determination of values of BIS/BAS response within individuals.

BACKGROUND OF INVENTION

An electroencephalograph (EEG) is a device used in electroencephalography; it records a set of weak electrical signals collected simultaneously from different points of a scalp using electrodes. The signals read by the electroencephalograph, known as EEG signals, mainly reflect the activity of brain neurons located beneath the electrodes. The EEG can help to examine the direct activity of groups of neurons and can be used clinically, e.g. to study epilepsy or sleep. Neuroscientific literature that describes neuroscientific indicators, studying memory, attention, emotions, language processing etc. relates mainly to ERP (Event Related Potential) or frequency analysis. The known frequency analysis techniques utilize mainly full frequency ranges, such as the Delta (1-4 Hz), Theta (4-8 Hz), Alpha (8-12 Hz, sometimes low alpha 8-10 Hz, and high 10-12 Hz), Beta (12-30 Hz, sometimes divided into low 12-15 Hz, medium 16-20 Hz and high 20-30 Hz) and Gamma (30~70 Hz) or frequency ranges close to these full frequency ranges.

Depending on the location of the electrodes, each of the frequency ranges is related to different types of processes, e.g. alpha frequencies in most locations are regarded as being indicative of reduced activity of each working region, and beta or gamma frequencies are regarded as being representative of increased activity of the region. This is confirmed by the studies carried out jointly by means of EEG and fMRI (ang. Functional Magnetic Resonance Imaging), for example as described in "EEG Correlated fMRI of human alpha activity" (H. Laufs et al., Neuroimage 2003 August; 19(4) pp. 1463-76).

Each region of the brain is responsible for a slightly different function, so the signal strength of a particular region is associated with the functions related to that region.

In the past, emotion studies performed using neuroscience tools were based mainly on GSR (Galvanic skin response) and EMG (Electromyography). Recently, emotion studies have been dominated in the scientific community by fMRI. EEG is the most popular device used for non-scientific applications and allows to measure BIS/BAS responses based on the amplitude of alpha waves in the prefrontal cortex.

BIS/BAS theory by J. A. Gray describes two systems responsible for emotions. BIS (Behavioral Inhibition System) is repulsing-aversion, disappointment, surprise, and BAS (Behavioural Activation System) is attraction—exploration, enjoyment, focus.

One algorithm for calculating the BIS/BAS response is described in the publication "Prefrontal brain asymmetry: A biological substrate of the behavioural approach and inhibition systems" (S. K. Sutton et al., Psychological Science, May 1997 vol. 8 no. 3, pp. 204-210).

Figure 1:
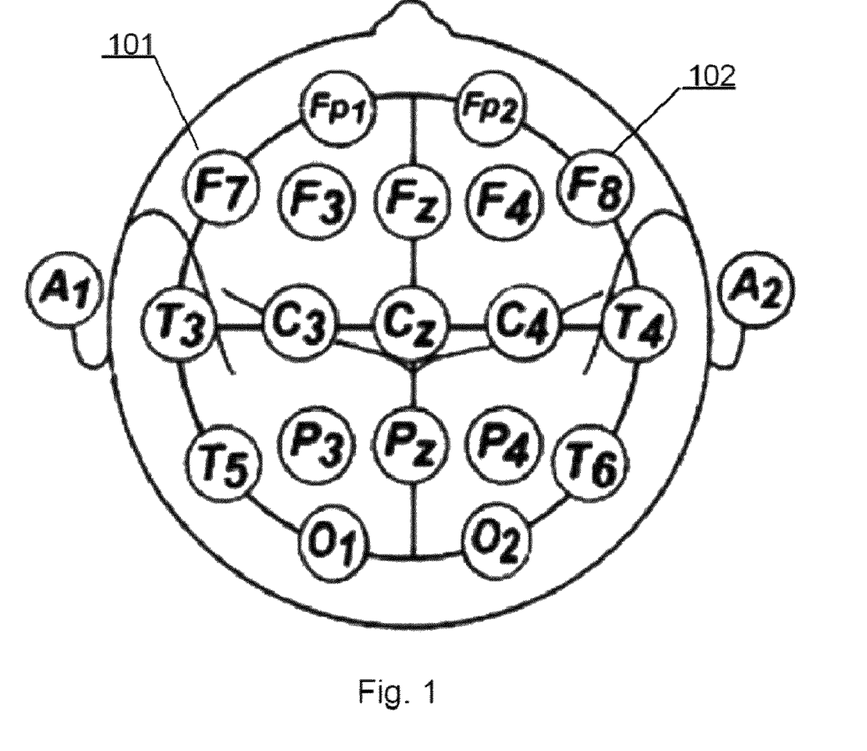
FIG. 1 shows a schematic arrangement of electrodes in accordance with the 10-20 system.

To measure the BIS/BAS indicator, the signal is collected from the electrodes F7 and F8 or F3 and F4 of the International 10-20 system (International 10-20 Electrode Placement System), defining the method of description and location of EEG electrodes on the scalp, as shown in FIG. 1.

This signal is high-pass and low-pass filtered to remove network artefacts and artefacts related to low oscillations. Then, the signal is cleared off muscle artefacts and time segments of a selected length are converted from the time domain to the frequency domain. Then, from the logarithm of the frequency power from the right electrode (F4 or F8), the logarithm value of the frequency power from the left electrode (F3 or F7) for alpha frequency (8-12 Hz) is deducted:

$$F34L\_alfa = \log(F4\_alfapower) - \log(F3\_alfapower)$$

A positive resulting value indicates a BAS response, and a negative value indicates a BIS response.

As the BIS/BAS response is increasingly being used in non-scientific applications, for example in devices for neuromarketing, biofeedback testing or in various types of devices for consumers, there is a need for an efficient and reliable method to measure it.

Due to the fact that the original measurement of BIS/BAS response is performed for the alpha frequency, it is very susceptible to ocular artefacts and other processes manifested by extinction in the prefrontal cortex.

Taking into account the techniques known in the prior art, there is a need for an alternative, effective method for measurement and interpretation of BIS/BAS response read by the electroencephalograph.

The existing methods for obtaining information about BIS/BAS responses have so low reliability of the results that they do not provide reliable results for a specific examined person. This is particularly important when using this method in consumer products, where it is impossible to determine the response of the individual consumer based on the average results of the study group.

SUMMARY OF INVENTION

Thus, the main aim of the present invention is to provide an alternative to the known prior art methods and systems for measurement and interpretation of BIS/BAS response read by an electroencephalograph, and in particular a method and system that will allow for accurate determination of BIS/BAS response within individuals.

The present invention is related to a method for processing EEG signals, the method comprising: reading the EEG signals from two frontal electrodes of an electroencephalograph; converting the EEG signals to a frequency domain; and determining values of a BIS/BAS response on the basis of an asymmetry between the EEG signals. The method comprises calculating the asymmetry between the EEG signals in the frequency domain in a frequency range from 26 to 29 Hz.

The method may comprise determining values of a BIS/BAS response on the basis of an asymmetry between the EEG signals in the frequency domain in a frequency range from 27 to 28.5 Hz.

The method may comprise calculating the value of the asymmetry as a difference between a normalized amplitude of the EEG signal from one electrode and a normalized amplitude of the EEG signal from the second electrode.

The method may comprise calculating the normalized amplitude of the EEG signals as:

$$Z_{Hz,t}=(x_{Hz,t}-\mu_{Hz})/\sigma_{Hz}$$

wherein:

z is the normalized value for a selected frequency (Hz) and a given time moment (t);

x is an original value for the selected frequency (Hz) and the given time moment (t);

µ is an average for the normalized segment for the selected frequency (Hz);

σ is a standard deviation for the selected frequency (Hz).

The present invention is also related to a method for processing EEG signals, the method comprising reading the EEG signals from two frontal electrodes of an electroencephalograph; converting the EEG signals to a frequency domain; and determining values of a BIS/BAS response on the basis of an asymmetry between the EEG signals. The method comprises calculating the asymmetry between the EEG signals as a difference between a normalized amplitude of the EEG signal from one electrode and a normalized amplitude of the EEG signal from the second electrode.

The method may comprise calculating the normalized amplitude of the EEG signal as:

$$Z_{Hz,t}=(x_{Hz,t}-\mu_{Hz})/\sigma_{Hz}$$

where:

z is the normalized value for a selected frequency (Hz) and a given time moment (t);

x is an original value for the selected frequency (Hz) and the given time moment (t);

σ is the average for the normalized segment for the selected frequency (Hz);

o is a standard deviation for the selected frequency (Hz).

The method may comprise determining the values of the BIS/BAS response on the basis of the asymmetry in the frequency domain between the EEG signals in a frequency range from 26 to 29 Hz, or preferably from 27 to 28.5 Hz.

Any of the methods described above may further comprise low-pass filtering or high-pass filtering the EEG signal before converting the signal to the frequency domain.

The methods may comprise low-pass filtering the EEG signal before converting the EEG signal to the frequency domain if the EEG signal comprises interferences in a frequency higher than half of the sampling frequency according to the Nyquist's theory.

The methods may comprise low-pass filtering the EEG signal before converting the EEG signal to the frequency domain if the EEG signal comprises a peak at a frequency of 50 or 60 Hz.

The methods may comprise converting the EEG signal to the frequency domain using a Fast Fourier Transform.

The methods may comprise reading the signal from electrodes F7 and F8 or electrodes F3 and F4 or electrodes Fp1 and Fp2 or from a vicinity thereof, according to the 10-20 system. In further embodiment the reference for selected electrodes may be ears electrodes.

The methods may further comprise removing artefacts from the EEG signal on the basis of EMG signals, EEG signals or body movements, before converting the EEG signal to the frequency domain.

The time window for the EEG signal for determining the BIS/BAS response may have a length of less than 2 seconds.

The invention is also related to a computer program comprising program code means for performing all the steps of the computer-implemented method as described above, as well as to a computer readable medium storing computer-executable instructions performing all the steps of the computer-implemented method as described above when executed on a computer.

The invention is further related to a system for processing EEG signals, the system comprising: an interface (1108, 1201) configured to read EEG signals from two frontal electrodes of an electroencephalograph; a converter (1109, 1209) configured to convert the EEG signals to a frequency domain; and a BIS/BAS response detector (1103, 1216) configured to determine values of a BIS/BAS response on the basis of an asymmetry between the EEG signals. The BIS/BAS response detector (1103, 1216) is configured to calculate the asymmetry between the EEG signals in the frequency domain in a frequency range from 26 to 29 Hz.

The invention is also related to a system for processing EEG signals, the system comprising: an interface (1108, 1201) configured to read EEG signals from two frontal electrodes of an electroencephalograph; a converter (1109, 1209) configured to convert the EEG signals to a frequency domain; and a BIS/BAS response detector (1103, 1216) configured to determine values of a BIS/BAS response on the basis of an asymmetry between the EEG signals. The BIS/BAS response detector (1103, 1216) is configured to calculate the asymmetry between the EEG signals as a difference between a normalized amplitude of the EEG signal from one electrode and a normalized amplitude of the EEG signal from the second electrode.

DETAILED DESCRIPTION

The aims of the invention disclosed herein are achieved by a computer-implemented method and system for processing the signal read by the electroencephalograph. Further details and features of the present invention, its nature and advantages will become clear from the following the following description of preferred embodiments shown in the drawing, in which.

The present invention relates to analysis of EEG signals and processing the EEG signals to calculate a BIS/BAS response indicator.

The EEG signal is collected from the prefrontal cortex, for example, from at least two electrodes. Preferably, the signal is received from pairs of electrodes F3, F4 or F7, F8 or Fp1, Fp2 (or their vicinity) according to the 10-20 system, in accordance with the arrangement shown in FIG. 1.

The measurement should be made by the electrodes located in the corresponding, opposing positions on the scalp, for example, positions F3 and F4 or positions F7 and F8.

A reference for the electrodes may be ear electrodes, as in the example shown, but this effect can also be achieved with other references, such as a reference to the average in the case of using a symmetrical assembly of electrodes, a Laplace reference in the case of using more electrodes or a reference to a central electrode FCz (if used). In the context of the use of the ear reference, it can be performed independently for each electrode relative to the proximal ear or to the combined references from both ears, which is especially convenient when using more electrodes.

Thus, a reference underlining the differences between the activity beneath the mentioned electrodes (electrode pairs) is required. Thus, the circular reference is not suitable, since the electrodes close to the specified ones carry a large amount of information.

Because the value of the EEG signal represents the difference between voltages on two electrodes, the reading of an electroencephalograph can be configured in one of several ways. Representation of EEG channels is usually referred to as an installation.

There are several types of installations: sequential, Laplace and reference, wherein each channel corresponds to the difference between a particular electrode and the designated reference electrode. There is no standard position for the reference electrode, but it should be located in a different place than the reading electrode. Positions of the center line are often used because they do not enhance the signal of one hemisphere relative to the other. Another common reference is the so-called "linked ears" reference, which is the average physical or mathematical coefficient of the signal of the electrodes attached to both ears or mastoid processes.

The method can be based both on clean signals obtained from the selected electrodes, as well as on their composite results resulting from addition/subtraction, or other means for receipt of a signal from the other electrodes, for example as a weighted average of selected weights of the electrodes F3, F7, Fp1 minus the values of electrodes placed on the main generators of the artefacts, such as for example the facial muscles (e.g. corrugator, frontalis, orbicularis), neck, heart.

In a preferred embodiment, the reference electrode is placed on both ears to provide suitable resistance.

The method of the present invention may also be based on the results obtained through the analysis of the signal sources or specific models assuming the use of more electrodes or a different set of electrodes, but referring to a source that is best recognizable beneath said electrodes without such analysis.

In a preferred embodiment, the signal from each electrode is normalized and free of artefacts (interferences) or at least their impact on a significant part of the signal is minimised. This can be achieved by using signal correction on the basis of the muscle activity using EMG and/or EEG, body movements using, for example, an accelerometer or a camera. It can also be achieved by analysis of the sources and consequently removing the sources of artefacts.

Preferably, the signal received from the electrodes is filtered. Depending on the techniques of processing the signal from the time domain to the frequency domain, low-pass and/or high-pass filters corresponding to this technique are used.

In a preferred embodiment, a high-pass filter with a passband of 1 Hz and a low-pass filter with a passband in the range of 35-70 Hz are used. A low-pass filter is necessary, which can be used before or during the conversion of analogue signal to a digital signal.

When using Fast Fourier Transform (FFT), a high-pass filter of about 1 Hz or below should be used. A notch filter can be used as well, to cut off the local value of the DC power (for example: 50 Hz in Europe, 60 Hz in the USA) or a low-pass filter about 43-45 Hz. These filter parameters are suitable for the FFT, as they allow eliminating the adverse effect of direct current on the read signal.

Figure 2:
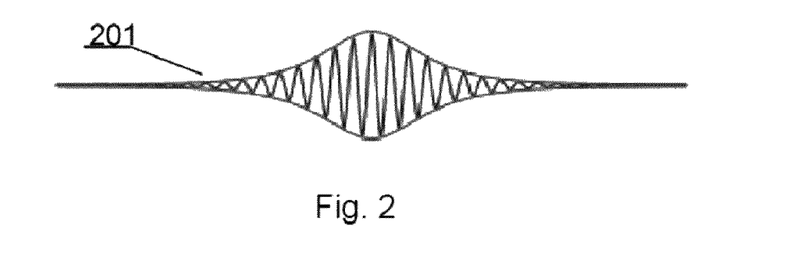
FIG. 2 shows an example of an envelope on an absolute value of the signal.

This processed signal is then converted to the frequency domain. This can be done for example by using the FFT or equivalent method, but also by using a high-pass and a low-pass filter from 26 to 29 Hz, more preferably from 27 to 28.5 Hz. Information on amplitude can be obtained for example by calculating the envelope of the absolute value of the filtered signal (which is a smooth curve emphasizing the extreme values of the signal amplitude, as for example shown in FIG. 2).

Figure 8:
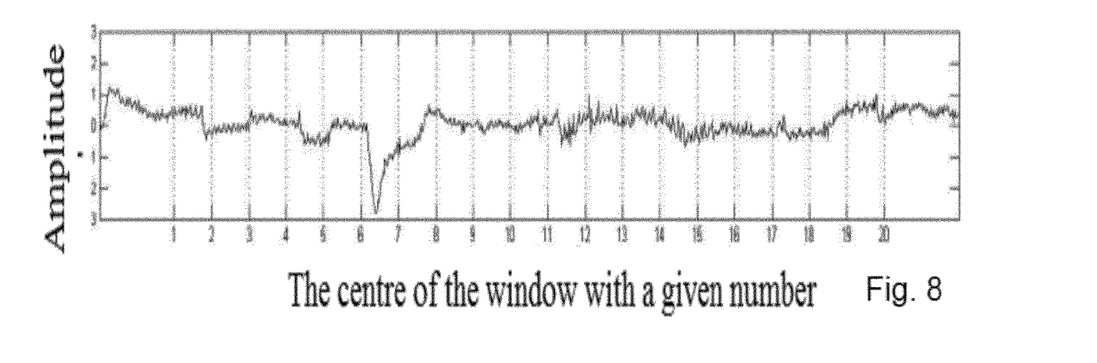

When the signal is converted from the time domain to the frequency domain, a single result is obtained and information on time is lost. It should be emphasized that performing such conversion on subsequent overlapping short time segments allows to keep some information about the time—thus, for example, FIG. 8 shows not a single value for the frequency, but continuous frequency graph of amplitudes for subsequent segments.

The above-mentioned envelope is related to that after using the low-pass filter and the high-pass filter, only a portion of the signal responsible for the selected frequency remains. Thus, by calculating the integral of the signal or calculating the envelope of the signal (which is simpler), a value is obtained that is close to the value of the frequency amplitude that could be obtained by other methods, such as FFT.

Due to the narrow frequency range used to calculate the indicator described herein, i.e. from 26 to 29 Hz, and preferably from 27 to 28.5 Hz, it is important to use a method with a high precision related to frequency. Therefore, FFT and wavelet algorithms or their precise counterparts, are optimal and preferred to be used in the embodiment of the invention.

The time window, based on which the amplitude value is calculated, depends on a particular application, but it should be relatively short (preferably, for example, less than 2 seconds), if it is to be used to study the BIS/BAS response as the emotion. Depending on the length of the windows, different types of responses are measured. For example, it is assumed in prior art literature that the level of asymmetry which is maintained over a longer period (e.g. two months) may be considered as a personality characteristics. On the other hand, emotions, by definition, are very short responses, usually lasting less than a second or a little more. Therefore, in the embodiment presented herein different ways of using the asymmetry index are shown, depending on the time for which it was measured and a method of efficient measurement and representation, retaining most of the information. In the case of the BIS/BAS model understood as an emotion, the window having a length of about 2 seconds or less should be used.

The values of the amplitudes of the selected frequencies should be normalized with respect to time, for example using the formula:

$$z = \frac{x - \mu}{\sigma}$$

$$z_{Hz,t} = (x_{Hz,t} - \mu_{Hz,t})/\sigma_{Hz}$$

wherein:

z is the normalised value for a selected frequency (Hz) and a given time moment (t);

x is an original value for the selected frequency (Hz) and the given time moment (t);

μ is an average or other central value for the normalized segment for the selected frequency (Hz);

σ is a standard deviation or another measure of dispersion for the selected frequency (Hz).

For the selected length of time, a value of the normalized frequency from the range of 26 to 29 Hz and preferably from 27 to 28.5 Hz should be selected for the left and right electrode and their values should be averaged for each electrode (e.g. using a median). Then, the resultant value for the right electrode should be subtracted from the left electrode. A positive value indicates the reaction of attraction and a negative value indicates the reaction of a repulsion.

It is noted that the application of the study for the selected narrow frequency range, i.e. from 26 to 29 Hz, and preferably from 27 to 28.5 Hz, allows to obtain better results than with the previously used study in the alpha frequency range. The inventors found that the alpha frequency is much more disturbed by the most common artefacts, i.e. ocular artefacts. This is particularly important in non-laboratory solutions, where the signal cannot be cleaned manually, as well as when smaller signal loss is desired. The inventors found that the ocular artefacts occur mainly at high frequencies (as most muscle movements, they can be observed best above 30 Hz) and low frequencies (depending on the person, up to 8-16 Hz). The inventors found that high-beta frequencies are characterized by high resistance to artefacts and a lower indicator of false results compared to the alpha frequency. The inventors found that the best signal quality is obtained for the range from 26 to 29 Hz, and preferably from 27 to 28.5 Hz.

Figure 3:
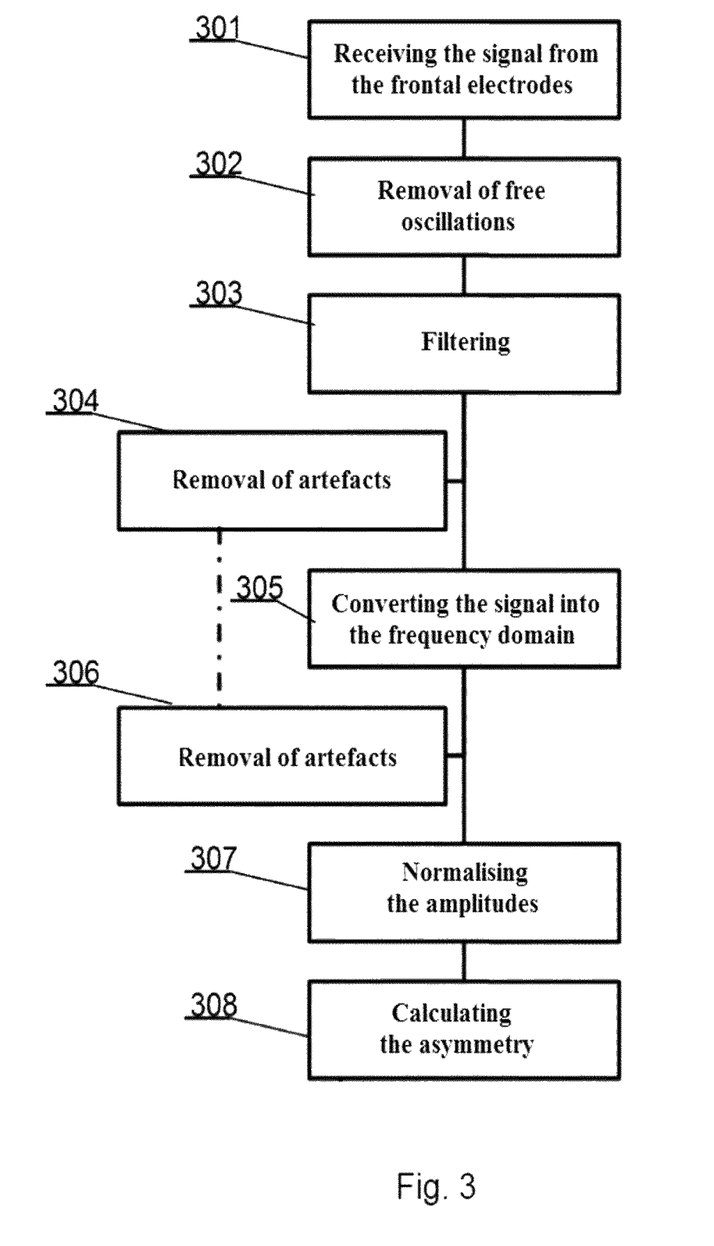
FIG. 3 shows a diagram of a method for processing EEG signals.

FIG. 3 shows a diagram of a method for processing EEG signals The procedure starts at step 301 by receiving the EEG signal from at least two frontal electrodes 301 symmetrically spaced from each on the right and the left half of the head. Then at step 302 free oscillations are removed, using a high-pass filter, i.e. oscillations of artefacts related for example to perspiration of the skin under the electrode, its movement and other factors.

The next step 303 comprises verifying whether the signal needs to be filtered and, if necessary, filtering is applied as previously described with respect to the low-pass filters and/or the high-pass filters. For example, a low-pass filter should be used if the interferences are present in a frequency higher than half of the sampling frequency according to the Nyquist's theory or if there is a peak for the mains frequency (50 or 60 Hz).

Further, in step 304, the artefacts are removed as described above. Alternatively, the artefacts may be removed in step 306.

In step 305 the signal is converted to the frequency domain. As described earlier, this can be done for example by using the FFT. The next step 307 of the procedure is to normalise the amplitude to perform the calculation of the asymmetry as the difference between the normalised amplitude of the one electrode (for example F3) and the normalized amplitude of the second electrode (e.g. F4) in step 308.

Figure 4:
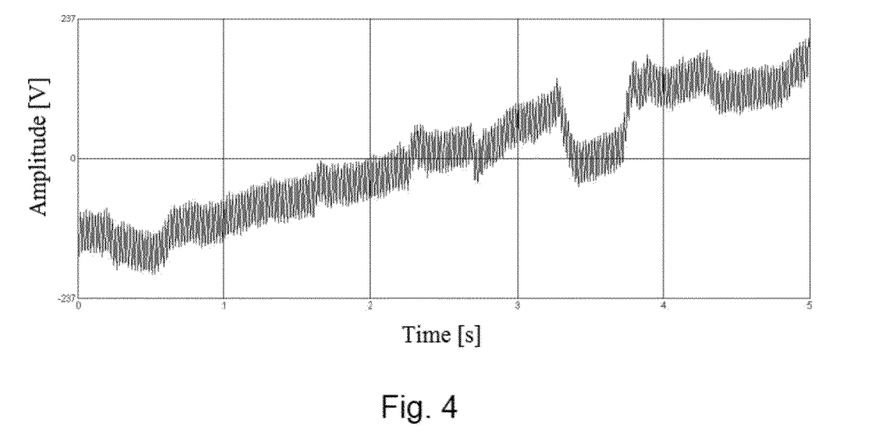
FIG. 4 shows a typical single EEG electrode signal with a lot of noise.
Figure 5:
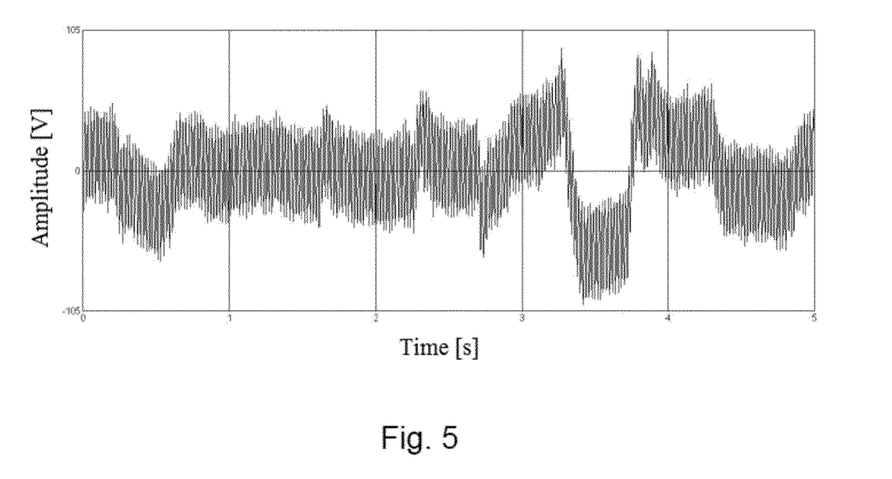
FIG. 5 shows the signal of FIG. 4 after application of a high-pass FIR filter with a cut-off frequency of 1 Hz.

FIG. 4 shows a typical original single EEG electrode signal with a lot of noise;

FIG. 5 shows an original signal of FIG. 4 after application of an exemplary high-pass FIR filter with a cut-off frequency of 1 Hz.

Figure 6:
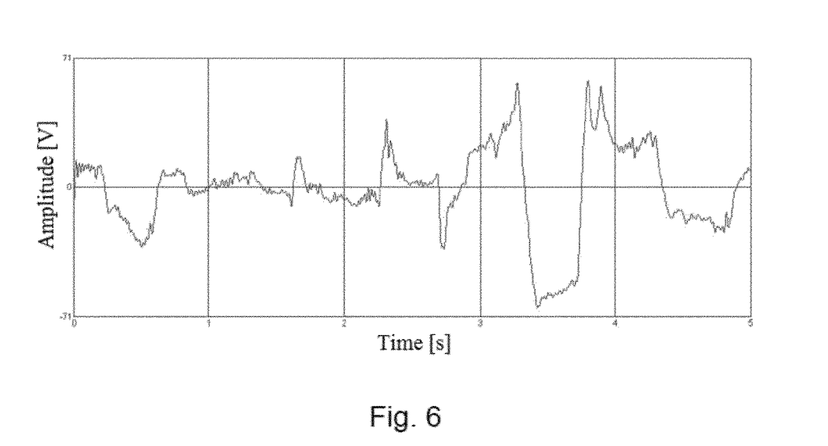
FIG. 6 shows an original signal processed with a band pass FIR filter with a range of 1-44 Hz.

FIG. 6 shows the original signal after using bandpass FIR filter with a range of 1-44 Hz.

Figure 7:
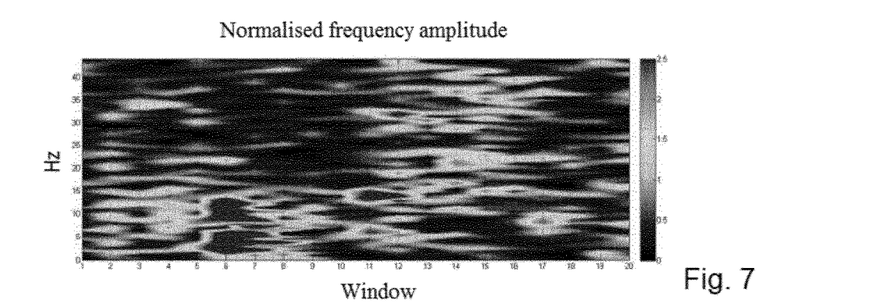
FIG. 7 and FIG. 8 shows a conversion of a signal from the time domain to the frequency domain.

FIG. 7 and FIG. 8 show the conversion of the signal from the time domain to the frequency domain. FIG. 7 shows an exemplary signal from the frontal electrode, filtered by an FIR high-pass filter at the frequency of 1 Hz, normalized relative to the entire study (12 minutes). FIG. 8 shows the value of the amplitude for frequencies between 1 and 44 Hz for each window based on the signal of FIG. 7. As before, the signal of FIG. 7 is a clean signal from a selected range, and the signal of FIG. 8 is a representation of frequencies therein for 1 s windows.

Figure 9A:
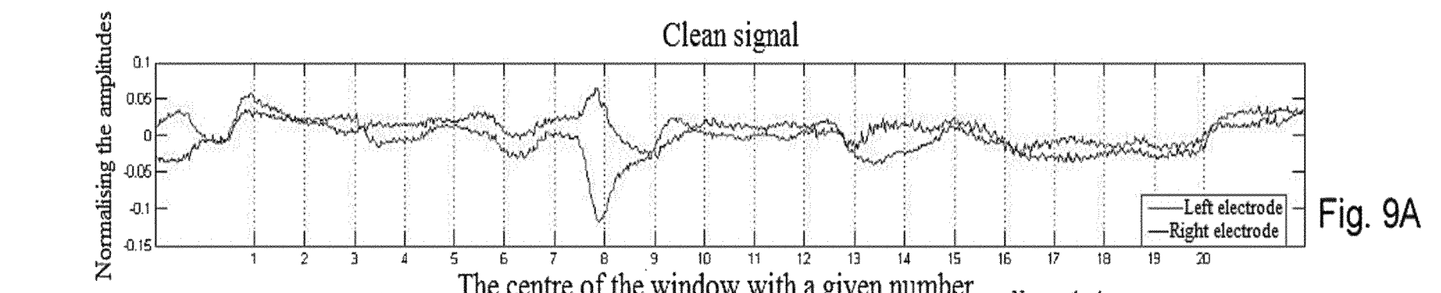
FIG. 9 shows a clean, filtered signals from the left and right electrode.
Figure 9B:
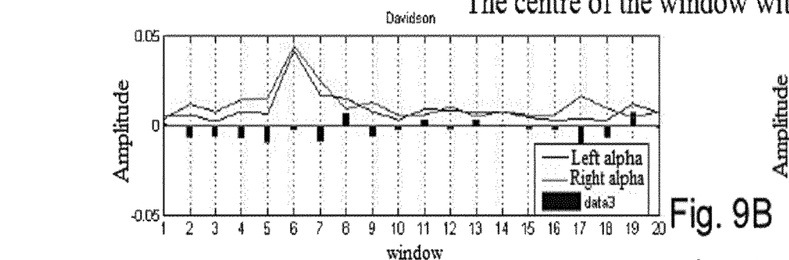
Figure 9C:
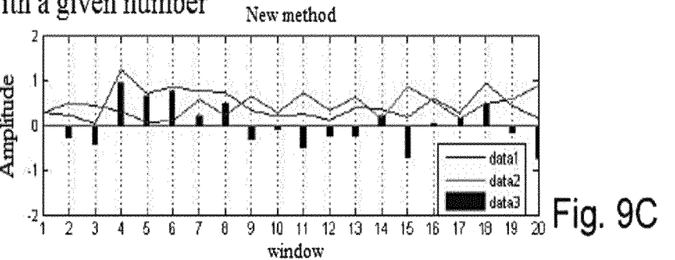
Figure 9D:
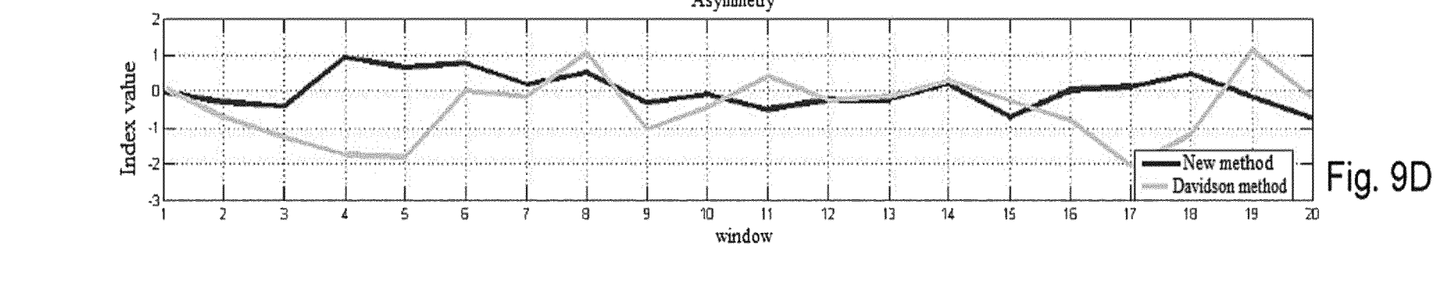

FIG. 9A shows a clean, filtered signal from the left and right electrodes. FIG. 9B shows the value of the amplitude for alpha frequencies for each window on the left and right electrode and on the bar graph amplitude differences between the right electrode and the left electrode, according to the approach described by Davidson. FIG. 9C shows the value of the normalized amplitude for a frequency range for each window on the left electrode and for right electrode and on the bar graph it shows amplitude differences between the right electrode and the left electrode for frequencies in the range 27-28.5 Hz, according to the approach of the invention. FIG. 9D shows a typical BIS/BAS reading based on a Davidson formula (with the logarithms of the signal power) and, for comparison, the corrected reading using a method according to the invention (new method). As shown in FIG. 9D, the results obtained by the method according to the invention are stable and present a low indicator value when the amplitude of both electrodes is low, as opposed to the Davidson indicator. By using a narrow band that is resistant to artefacts, the indicator of the invention rarely shows a false result (usually high due to the characteristics of the artefacts in the EEG). Furthermore, by using the difference instead of the ratio (as in the Davidson indicator) for two low values, the result is always low (as opposed to a Davidson indicator).

FIGS. 10A-10F shows graphs indicating the behaviour of the equations used to calculate the asymmetry. The size of the dot is the value of asymmetry index according to the equation above the graph. The X axis is the value of the amplitude of the frequency of the left electrode and the Y-axis is the value of the amplitude of the frequency of the right electrode. Bright spots represent positive responses and the dark dots indicate negative responses.

Figure 10A:
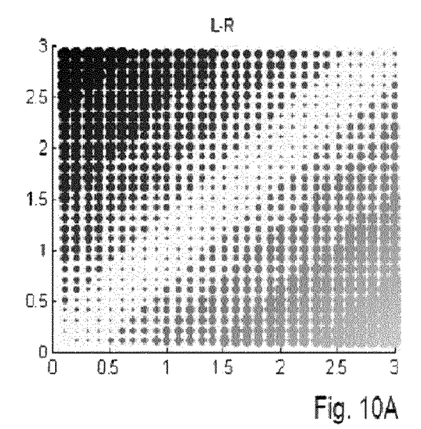
FIG. 10 shows graphs indicating the behavior of the equations used to calculate the asymmetry; it shows the asymmetry index value for the two models used for its calculation in versions with an average amplitude, logarithm amplitude and amplitude root.
Figure 10B:
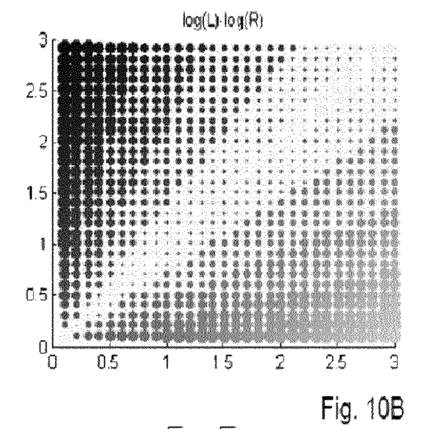
Figure 10C:
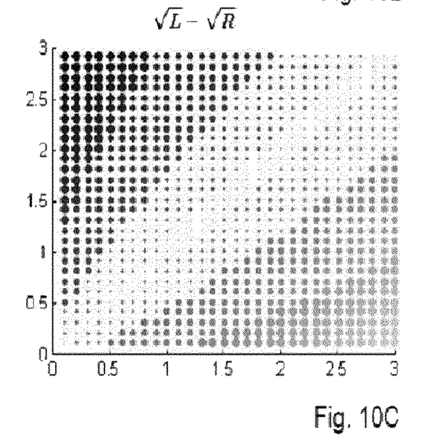
Figure 10D:
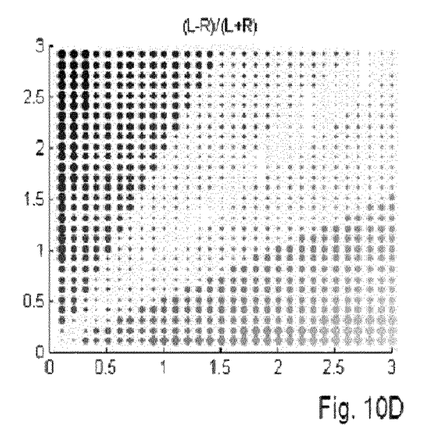
Figure 10E:
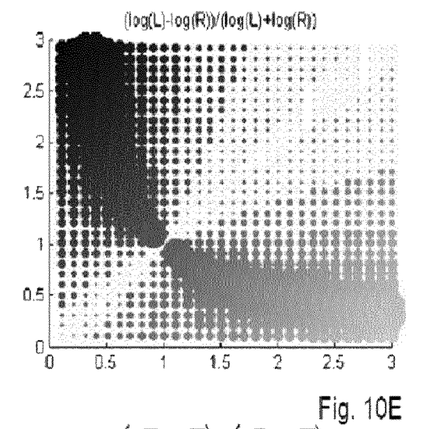
Figure 10F:
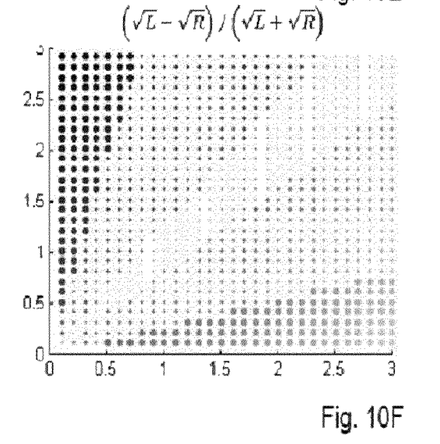

FIGS. 10A, 10B, 10C relate to the asymmetry, which is the difference between the left and right electrode. FIGS. 10D, 10E, 10F relate to the asymmetry divided by the sum of both electrodes. FIGS. 10A, 10D do not contain any changes, FIGS. 10B, 10E relate to the equations using logarithms, and FIGS. 10C, 10F relate to the equations using the root.

The solution according to the invention is illustrated in FIG. 10A, which illustrates the behaviour of the equation performed in step 308 of the method.

The solution according to the standard from Davidson works was illustrated in FIG. 10B.

Other FIGS. 10C-10F illustrate other alternative calculations. FIG. 10E has a singularity associated with the possibility of the creation of zero in the denominator.

As shown in FIG. 10A and compared to FIGS. 10B-10F, the solution according to the invention provides the most proportional results. The other graphs show that too much importance has been attributed to the extreme results.

In contrast, the best results can be achieved using the formula of FIG. 10A, in step 308, when tested at frequencies in the range of 26 to 29 Hz, and preferably from 27 to 28.5 Hz, thus obtaining the results of the benefits discussed above with respect to FIG. 9D.

Figure 11:
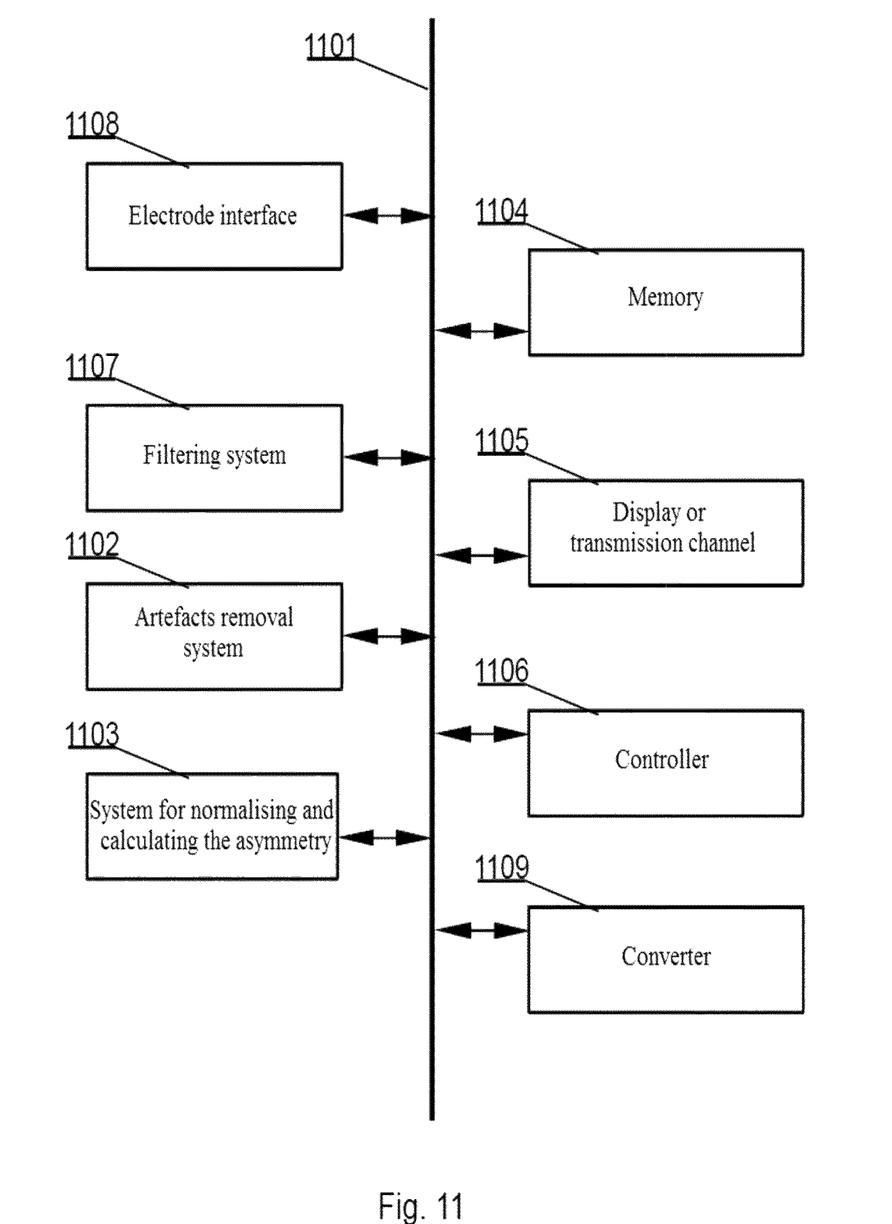
FIG. 11 shows a system of the invention.

FIG. 11 shows one embodiment of the system according to the invention. The system can be implemented by means of dedicated components or custom-designed FPGA or ASIC modules. The system includes a data bus 1101 communicatively connected to a memory 1104. It has an output data memory configured for example to save data received from electrodes 1108, as well as to store computer programs executed by a controller 1106.

In addition, the other configurations of the system according to the present invention are communicatively connected to the system bus 1101, to be managed by the main controller 1106.

The system includes an interface 1108 for reading the EEG signals from the electrodes, for example an RS232 interface.

Additionally, the system comprises a filtering module 1107 configured to perform step 303 of the method according to the present invention and an artefacts removing module 1102 configured to perform step 304/306 of the method according to the present invention.

Another element of the system is a signal converter 1109 for converting the signal to the frequency domain, for example, a module for computing FFT at the execution of step 305 of the method.

Moreover, the system comprises a module for normalizing and calculating the asymmetry 1103 configured to perform steps 307-308 of the method according to the present invention.

Another element of the exemplary system is a display module or a transmission channel 1105. In one embodiment, the system has a built-in or connected display for presenting the results of signal processing according to the present invention. In the case where there is no display and it cannot be directly connected, the system may send the results to another device intended for the presentation of results or for performing an action.

Figure 12:
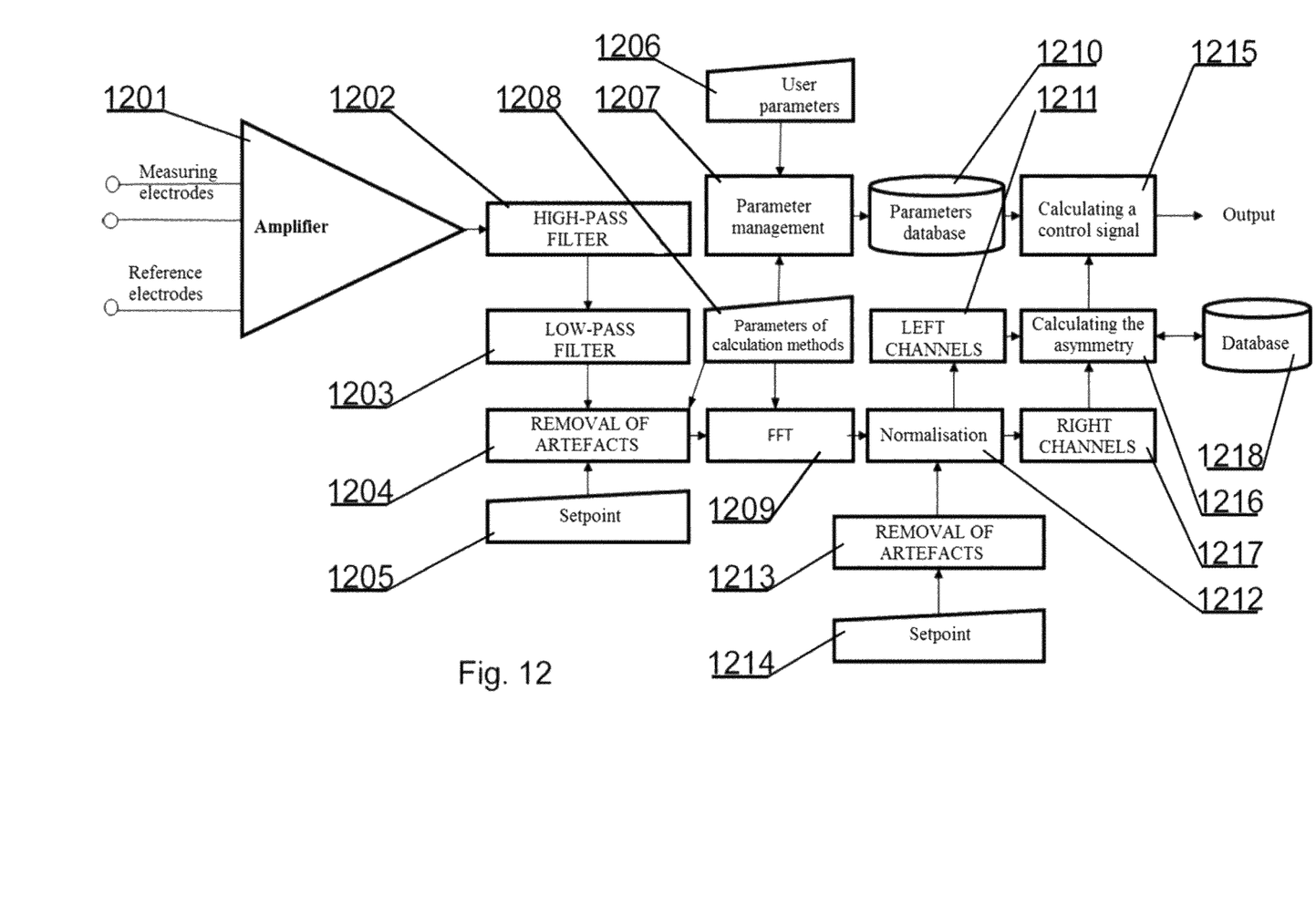
FIG. 12 shows another embodiment of the system according to the invention.

FIG. 12 shows another embodiment of the system according to the invention. The system comprises an amplifier 1201, which is the interface to which the measurement electrodes of the electroencephalograph are attached, in particular two frontal electrodes and/or a reference electrode. The outputs of the amplifier (separately transmitting signals from individual electrodes, but shown for simplicity by a single line in the drawing) are connected to a set of filters 1202, 1203: a high-pass filter 1202 and a low-pass filter 1203, which are connected to an artefacts removal module 1204, which is controlled by a regulator 1205 (the value of which can be set manually or automatically) or using a module 1208. The module 1208 allows to determine various kinds of parameters for controlling the operation of the other modules. The output signals from the artefacts removal module 1204 are connected to the module for converting the signal to the frequency domain, for example, FFT module 1209, the output of which is connected to a normalising circuit 1212, configured to process the signal in accordance with the normalisation method described above. Also, the operation of the module 1209 can be controlled using the module 1208. Normalised signals, after optional further removal of artefacts by the module 1213 controlled by the regulator 1214, are allocated to a left channel 1211 and a right channel 1217, and then fed to an asymmetry calculating module 1216, configured to calculate the asymmetry in accordance with the method described above. Data on asymmetry may be stored in a database 1218. A module 1215 calculates the control signal, that is, the value of BIS/BAS indicator on the basis of information on the asymmetry calculated by the module 1216. The module 1206 is a module accepting the parameters from the user and allows to control the scope of the parameters and rules controlling the control signal 1215. For example, the module 1206 can determine what shall be done for particular values of asymmetry trigger signal, e.g. to take a photo. The module 1210 is a memory that stores the rules for generating a control signal given by the user, as well as the rules embedded and specified by the manufacturer of the device or other external unit with licenses. The module 1207 is a module that converts the parameters specified by the user and the external units into those appropriate for the user and specific device model.

The application of the method and system of the invention include neuromarketing, assessment of audio and video materials including videos, photographs, drawings, multimedia presentations etc., assessment of taste and smell, assessment of facilities. For example, it can be used for assessment of a shop by mapping of attraction/repulsion in a 3D space based on the submission of EEG signals and corresponding data from an eye tracker, a computer mouse or other control devices, a position in a virtual space, a position in a real space (e.g. indicated by a GPS or an accelerometer, WiFi, GSM/LTE/CDMA and the like).

Furthermore, the invention is useful for assessment of enjoyment of interactions in games, of Internet portals and of quality of use of computer software.

The present invention is applicable also in daily use, for example for presenting emotional state changes over time, for detecting abnormal events in the life of the user based on the frequency of the extreme values of the indicator.

Another class of applications is to use the indicator to control other devices, e.g. a camera and/or a microphone (e.g. taking a photo, video, audio, turning on an alarm or sending a notification) as well as startup and shutdown of the applications preselected by the user or pre-programmed on the phone, tablet, other type of computer when the value of the asymmetry index is at a level/range selected or declared by the user. This also applies to the use of a device equipped with the present invention as a software controller, e. g. of games both as an active controller triggering the options or activity actions etc., selected by the creator of the game or the player, or a passive one allowing to choose the level of the game, setting the characters, scenery or appearance of the character or surrounding.

In combination with the eye tracking system, the invention can be used to start up the device/application/objects which the individual sees—when the value of the asymmetry index is at a level or range selected or declared by the user.

The method and the system are also applicable in the content recommendation systems as a tool for automatic cataloguing and assessing the content e.g. in the sales recommendation systems, search engines or social networking sites to recommend content, advertisements and friends in psychotherapy and for job interviews assessment.

One skilled in the art will appreciate that the described method for processing the signal read by the electroencephalograph may be performed and/or controlled by one or more computer programs. Such computer programs are typically executed by utilizing the computing resources in a computing device such as personal computers, personal digital assistants, cellular telephones, receivers and decoders of digital television or the like. Applications are stored in non-volatile memory, for example a flash memory or volatile memory, for example RAM and are executed by a processor. These memories are exemplary recording media for storing computer programs comprising computer-executable instructions performing all the steps of the computer-implemented method according the technical concept presented herein.

While the invention presented herein has been depicted, described, and has been defined with reference to particular preferred embodiments, such references and examples of implementation in the foregoing specification do not imply any limitation on the invention. It will, however, be evident that various modifications and changes may be made thereto without departing from the broader scope of the technical concept. The presented preferred embodiments are exemplary only, and are not exhaustive of the scope of the invention presented herein.

Accordingly, the scope of protection is not limited to the preferred embodiments but is limited by the appended claims.

The invention claimed is:

1. A method for processing EEG signals for a single patient having only a first electrode attached to the patient and a second electrode attached to the patient, the method comprising:
   reading the EEG signals from an electroencephalograph consisting of EEG signals from the first electrode and the second electrode;
   converting the EEG signals from only the first electrode and the second electrode to a frequency domain;
   determining values of a BIS/BAS response on a basis of an asymmetry between the EEG signal from only the first electrode and the EEG signal from only the second electrode;
   independently normalizing amplitude of the EEG signal from only the first electrode and only data from the single patient with respect to time in only a frequency domain in a frequency band from 26 to 29 Hz for a time segment, the independently normalizing comprising centering and scaling the data from the single patient with respect to time in only the frequency domain and the frequency band from 26 to 29 Hz for the time segment;
   independently normalizing amplitude of the EEG signal from only the second electrode and only data from the single patient with respect to time in only the frequency domain in the frequency band from 26 to 29 Hz for the time segment, the independently normalizing comprising centering and scaling the data from the single patient with respect to time in only the frequency domain and the frequency band from 26 to 29 Hz for the time segment;
   calculating asymmetry between the EEG signal from the first electrode and the EEG signal from the second electrode in the frequency domain in a frequency band from 26 to 29 Hz as a difference between the amplitude of a normalized frequency band of 26 to 29 Hz of the EEG signal from only the first electrode, and the amplitude of a normalized frequency band of 26 to 29 Hz of the EEG signal from only the second electrode.

2. The method according to claim 1, comprising determining values of the BIS/BAS response on the basis of the asymmetry between the EEG signals in the frequency domain in a frequency band from 27 to 28.5 Hz.

3. The method according to claim 1, further comprising low-pass filtering or high-pass filtering the EEG signals before converting the EEG signal to the frequency domain.

4. The method according to claim 3, comprising low-pass filtering the EEG signals before converting the EEG signals to the frequency domain if the EEG signals comprise interferences in a frequency higher than half of a sampling frequency according to Nyquist's theory.

5. The method according to claim 3, comprising low-pass filtering the EEG signals before converting the EEG signals to the frequency domain if the EEG signals comprise a peak at a frequency of 50 or 60 Hz.

6. The method according to claim 1, comprising converting the EEG signals to the frequency domain using a Fast Fourier Transform.

7. The method according to claim 1, comprising reading the EEG signals from electrodes F7 and F8 or electrodes F3 and F4 or electrodes Fp1 and Fp2 or from a vicinity thereof, according to a 10-20 system.

8. The method according to claim 7, wherein a reference for selected electrodes are ear electrodes.

9. The method according to claim 1, further comprising removing artefacts from the EEG signals on the basis of EMG signals, the EEG signals or body movements, before converting the EEG signal to the frequency domain.

10. The method according to claim 1, wherein the reading is performed in a time window having a length of less than 2 seconds.

11. A computer program comprising program code for performing all steps of the method according to claim 1 when said program is run on a computer.

12. A computer readable medium storing computer-executable instructions performing all steps of the method according to claim 1 when executed on a computer.

13. A method for processing EEG signals for a single patient having only a first electrode attached to the patient and a second electrode attached to the patient, the method comprising:
   reading the EEG signals from an electroencephalograph consisting of EEG signals from the first electrode and the second electrode;
   converting the EEG signals from only the first electrode and the second electrode to a frequency domain;
   determining values of a BIS/BAS response basis on an asymmetry between the EEG signal from only the first electrode and the EEG signal from only the second electrode;
   independently normalizing amplitude of the EEG signal from only the first electrode and only data from the single patient with respect to time in only the frequency domain in a frequency band from 26 to 29 Hz for a time segment, the independently normalizing comprising centering and scaling the data from the single patient with respect to time in only the frequency domain and the frequency band from 26 to 29 Hz for the time segment;
   independently normalizing amplitude of the EEG signal from only the second electrode and only data from the single patient with respect to time in only the frequency domain in the frequency band from 26 to 29 Hz for the time segment, the independently normalizing comprising centering and scaling the data from the single patient with respect to time in only the frequency domain and the frequency band from 26 to 29 Hz for the time segment;
   calculating the asymmetry between the EEG signal from the first electrode and the EEG signal from the second electrode in the frequency domain in the frequency band of 26 to 29 Hz as a difference between the amplitude of the normalized frequency band of 26 to 29 Hz of the EEG signal from only the first electrode, and the amplitude of the normalized frequency band of 26 to 29 Hz of the EEG signal from only the second electrode;

calculating the normalized amplitude of the EEG signals as:

$$Z_{Hz,t}=(X_{Hz,t}-\mu_{Hz})/\sigma_{Hz}$$

wherein:
z is a normalized value for a selected frequency (Hz) and at a given time moment (t);
x is an original value for the selected frequency (Hz) and at the given time moment (t);
μ is an average for the selected frequency (Hz);
σ is a standard deviation for the selected frequency (Hz).

14. A system for processing EEG signals, the system comprising:
an interface configured to read EEG signals from only a first frontal electrode and a second frontal electrode of an electroencephalograph, the first and second frontal electrodes configured to attach to a single patient;
a converter configured to convert the EEG signals from only the first electrode and the second electrode to a frequency domain; and
a BIS/BAS response detector configured to determine values of a BIS/BAS response on a basis of an asymmetry between the EEG signal from only the first electrode and the EEG signal from only the second electrode;

wherein the BIS/BAS response detector is configured to calculate the asymmetry between the EEG signal from the first electrode and the EEG signal from the second electrode in the frequency domain in a frequency band from 26 to 29 Hz as a difference between an amplitude of a normalized frequency band of 26 to 29 Hz of the EEG signal from only the first electrode and an amplitude of a normalized frequency band of 26 to 29 Hz of the EEG signal from only the second electrode;

wherein the BIS/BAS response detector is configured to independently normalize amplitude of the EEG signal from only the first electrode and only data from the single patient with respect to time in only the frequency domain in the frequency band from 26 to 29 Hz for a time segment, the independently normalizing comprising centering and scaling the data from the single patient with respect to time in only the frequency domain and the frequency band from 26 to 29 Hz for the time segment and wherein the BIS/BAS response detector is configured to independently normalize the EEG signal from only the second electrode and only data from the single patient with respect to time in only the frequency domain in the frequency band from 26 to 29 Hz for the time segment, the independently normalizing comprising centering and scaling the data from the single patient with respect to time in only the frequency domain and the frequency band from 26 to 29 Hz for the time segment.

* * * * *